(12) United States Patent
Wolinsky et al.

(10) Patent No.: US 9,161,787 B2
(45) Date of Patent: Oct. 20, 2015

(54) VERTEBRAL BODY REDUCTION INSTRUMENT AND METHODS RELATED THERETO

(75) Inventors: Jean-Paul Wolinsky, Baltimore, MD (US); Daniel Stoianovici, Reistertown, MD (US)

(73) Assignee: The Johns Hopkins University, Baltimore, MD (US)

( * ) Notice: Subject to any disclaimer, the term of this patent is extended or adjusted under 35 U.S.C. 154(b) by 344 days.

(21) Appl. No.: 12/766,481

(22) Filed: Apr. 23, 2010

(65) Prior Publication Data
US 2010/0274252 A1 Oct. 28, 2010

Related U.S. Application Data

(60) Provisional application No. 61/172,157, filed on Apr. 23, 2009, provisional application No. 61/265,065, filed on Nov. 30, 2009.

(51) Int. Cl.
*A61B 17/70* (2006.01)
(52) U.S. Cl.
CPC .................... *A61B 17/708* (2013.01)
(58) Field of Classification Search
CPC ..................................................... A61B 17/708
USPC ................................................. 606/90, 105
See application file for complete search history.

(56) References Cited

U.S. PATENT DOCUMENTS

| | | | |
|---|---|---|---|
| 5,005,562 A | 4/1991 | Cotrel | |
| 5,360,431 A | 11/1994 | Puno et al. | |
| 5,397,363 A | 3/1995 | Gelbard | |
| 5,616,143 A * | 4/1997 | Schlapfer et al. | 606/86 A |
| 6,139,548 A | 10/2000 | Errico | |
| 6,716,218 B2 * | 4/2004 | Holmes et al. | 606/105 |
| 2003/0225416 A1 * | 12/2003 | Bonvallet et al. | 606/105 |
| 2005/0245928 A1 * | 11/2005 | Colleran et al. | 606/61 |
| 2006/0009775 A1 * | 1/2006 | Dec et al. | 606/86 |
| 2007/0191856 A1 * | 8/2007 | Gil et al. | 606/90 |
| 2009/0204151 A1 | 8/2009 | Bracken | |
| 2010/0121386 A1 * | 5/2010 | Peultier et al. | 606/86 A |

* cited by examiner

*Primary Examiner* — David Bates
(74) *Attorney, Agent, or Firm* — Mintz Levin Cohn Ferris Glovsky and Popeo, P.C.; Peter F. Corless; Richard B. Emmons (57) ABSTRACT

Featured is a reduction instrument being configured and arranged to allow correction of vertebral translation and applying distraction across a segment in an independent fashion. Such a reduction instrument embodies one or more identical modules that are configured as needed for correcting the deformity. In more particular embodiments, each of the one or more modules has two degrees of freedom (DOF) with uncoupled orthogonal translations. Such a reduction instrument allows the reorientation of the vertebral segment as needed via uncoupled orthogonal translations. Such a reduction instrument also is usable in combination with a plurality of vertebral anchors, such vertebral anchors being any such vertebral anchors as are know to those skilled in the art (e.g., conventional spinal pedicle screw instrumentation) or hereinafter developed so as to form a spinal implant system. Also featured are treatment methods utilizing such a reduction instrument.

15 Claims, 7 Drawing Sheets

VERTEBRAL BODY REDUCTION INSTRUMENT AND METHODS RELATED THERETO

This application claims the benefit of U.S. Provisional Application Ser. No. 61/172,157 filed Apr. 23, 2009 and of U.S. Provisional Application Ser. No. 61/265,065 filed Nov. 30, 2009, the teachings of all of which are incorporated herein by reference in their entirety.

FIELD OF INVENTION

The present invention relates to methods for stabilization of the spine and spinal implants and instruments for use in such methods and more particularly to methods, implants and instruments for use in connection with surgical treatment strategies for the treatment of spondylolithesis and yet more particularly to a vertebral body reduction instrument for use in such methods, implants and treatment strategies.

BACKGROUND OF THE INVENTION

Spondylolithesis is a type of spinal deformity where one vertebral body is displaced relative to another adjacent vertebral body. There are a number of treatment strategies for spondylolithesis including non-surgical treatment strategies and surgical treatment strategies. While non-surgical treatment strategies are typically implemented first, the condition can worsen and the non-surgical strategies may not prove to be successful in given cases. Also, the severity of the condition may be such that the non-surgical strategies are practically speaking not a viable option.

Surgical treatment strategies for these deformities typically incorporate the concept of reduction of the spondylolithesis and stabilization of the segment. In the cases of prior treatment strategies and devices, stabilization of a segment has been accomplished with the use of various pedicle screw constructs. Because of limitations with prior devices, the reduction of the deformity has been a challenge, and all previous instruments have been unable to allow both correction of the translation as well as application of distraction across a segment in an independent fashion. In addition, known implant systems are typically designed and configured in such a way, that one system is not easily adaptable to use the means of another system.

There are presently a number of implant systems or spondylolithesis reduction instruments known to those skilled in the art, however, none of these instruments have the flexibility to allow reduction to be performed at any level and none can perform reduction in the cervical spine. In addition, none of the current instruments allow reduction to be performed with uncoupled control of translation and distraction/compression.

One of the instruments currently available for spondylolithesis reduction is the $S^4$ Spondylolithesis Reduction Instrument as made by Aesculap. Such an instrument or spinal system includes extended tabs whose small diameter and the polaxicity thereof maximize the range of the screw body to ease rod capture without the use of additional instruments. Such an instrument or implant system, however, does not allow reduction to be performed with uncoupled control of translation and distraction/compression.

There is described in U.S. Pat. No. 6,139,548 a sliding shaft variable length cross-link device that is for use with a dual rod apparatus such as that described in U.S. Pat. No. 5,005,562. Such a compression locking variable length cross-link device has a pair of rod hooking elements, each having rod securing and coupling ends. The coupling ends are slidably engaging by the insertion of one into the receiving socket of the other and for selective locking to one another independent of the relative separation of the rod securing ends. Each hooking element has a curvate end formed from flat material which has been shaped into a hook conformation to cup the lateral outside surface of a corresponding rod. A set screw positioned through a hole in the top of the curved end locks the curved end to the rod. In a first embodiment, one (a first) rod hooking element has a uniform cylindrical portion which may also include a knurled surface. The corresponding (second) element has a tubular portion including an axial receiving volume having an opening into which the cylindrical portion of the first element may be slidably inserted.

The exterior surface of the tubular portion of the second element includes a slotted, threaded and tapered tip which is wider at the end thereof. A nut may be engaged on the threads of the tubular portion and advanced onto the tapered portion thereof to cause the slots to narrow, crush locking the surfaces of the inner volume and the shaft together, thereby securing the two elements at a specific separation. Set screws may then be utilized to compress and lock the rods to the curved rod securing ends of each element.

There is described in U.S. Pat. No. 5,397,363, a surgical implant system for the stabilization of a human spine by fixation of the vertebra utilizing a stabilization cross-link spinal implant system. Such a system utilizes self-tapping screws having bifurcated protruding members to support an alignment rod, the protruding members available for placement of a fixed or variable traverse cross-link member that couples to the protruding members by use of threaded nuts corresponding to the threaded portion of the outer surface of the protruding members. The externally threaded coupling method can also be used for pedicle, caudal, cranial, thoracic and the like hooks. Also shown is a two plate system for anterior cervical spine fixation.

There is described in U.S. Pat. No. 5,360,431 an apparatus for the internal fixation of the spine. The apparatus includes two sets of implants each consisting of a rod and a plurality of vertebral anchors. The rod is secured to the vertebral elements by the vertebral anchors. The anchor includes a transpedicular screw which is secured to a vertebrae. The anchor further includes an anchor seat which captures the screw and permits micromotion between the anchor seat and the screw. This seat has a rod-receiving channel which captures the rod. A cap cooperates with the seat to secure the rod in the anchor. A nut screws down from the top of the assembly onto the seat to cause the rod receiving flanges in the cap to apply a compressive force to the rod. A method of therapy also is described in which the present implants are inserted surgically into a patient.

There is described in US Publication No. US 2009/0204151 a spinal implant procedure and system that includes vertical rods fastened to the spine on opposite sides. A cross connector is arranged on each vertical rod and to opposite ends of a cross member. The cross member includes a block having a lateral opening and that includes a forked end that is arranged at a bottom side of a spineous process. A strap fastener include openings through which the cross member passes. An opening of the strap fastener hooks on a catch on the side of the block. The block limits prevents rotation, blocks extension and limits flexion of the affected vertebrae.

It thus would be desirable to provide a new reduction instrument or device and methods for treating spondylolithesis using surgical techniques. It would be particularly desirable to provide such a device and method that would allow both correction of the translation as well as application of distraction across a segment in an independent fashion. Such devices/instruments preferably would be simple in construction and less costly than prior art devices and such methods would not require highly skilled users to utilize the device.

SUMMARY OF THE INVENTION

The present invention features a reduction instrument that is used in combination with a plurality of vertebral anchors, the vertebral anchors being any of a number of vertebral anchors as are known to those skilled in the art (e.g., spinal pedicle screw instrumentation) or hereinafter developed so to form a spinal implant system. Such a reduction instrument or device is configured and arranged so as to allow correction of the translation as well as application of distraction across a segment in an independent fashion. In further embodiments, such a reduction instrument or device embodies one or more identical modules that are configured as needed for correcting the deformity, and in more particular embodiments each instrument/device includes a plurality of such modules. In more particular embodiments, each of the at least one module or plurality of modules has two degrees of freedom (DOF) with uncoupled orthogonal translations.

Such a reduction instrument or device allows the reorientation of the vertebral segment as needed via uncoupled orthogonal translations. Thus, distraction/compression and translation of the vertebral bodies can be achieved using the reduction instrument/device and implant system of the present invention over a defined spinal segment. Such uncoupling of the orthogonal translations allows intuitive and controlled correction of a deformity.

In further embodiments, each module includes two separate assemblies—the base unit that is configured and arranged so as attach to a plurality of vertebral anchors, the vertebral anchors being any of a number of vertebral anchors as are known to those skilled in the art and hereinafter developed (hereinafter spinal implant), and the reduction instrument or primary device that controls the orthogonal translations. In exemplary embodiments, the base unit is configured and arranged so as to mate with the Depuy Expedium pedicle screw instrumentation system through the Viper V2 percutaneous extensions.

The reduction instrument or device is unique in that it is usable in combination with almost any currently available vertebral anchor. It also is usable with both "open" surgical procedures and percutaneous pedicle screw techniques. It allows a continuous adjustment and allows for manipulation of the vertebral segment to occur with intuitive uncoupled motion.

In further embodiments, the base unit includes two base elements, each base element including a threaded rod portion and a foot link at one end of the threaded rod. The foot link is configured an arranged so as to mate with the spinal implant. In exemplary embodiments, the foot link is configured and arranged to mate with the V-2 extension connected to the DePuy Expedium spinal implant.

The threaded rod portion is threaded along its length and in further embodiments, such a rod portion is a tubular member. As described further herein, the thread pitch of the threaded rod portion corresponds to the same thread pitch as that embodied in the primary device and the primary device threads onto the threaded rod portion base. In yet further embodiments, the thread pitch lends a mechanical advantage that allows the relative movement of the vertebral bodies.

In further embodiments, the primary device includes two portions that are connected to one another by two parallel sets of bars that are allowed to pivot in one plane around a central point forming a double 'X' configuration, a scissor mechanism. The primary device is configured and arranged so as to separately control both orthogonal translations, Translation-1 and Translation-2, that is provided by the primary device.

Depending how many and how the one or more modules are configured, placed, and oriented on the spine, the two translations or two DOF for each module can achieve a multi-degree of freedom correction. These can be used to correct distraction/compression and anterior/posterior translation. In a typical mounting situation, Translation-1 is aligned along the anterior/posterior translational direction and Translation-2 is along the distraction/compression direction.

Such a primary device also includes a first translation mechanism, that allows translation along the length of the rod portion of the base unit. Such a first translation mechanism includes two threaded structures, each of which threadably engages a respective threaded rod portion of the base unit, a plurality of a first sliding mechanisms that slidably couple the scissors mechanism and the two threaded structures and a plurality of support portions that operably couple the scissors mechanism and the two threaded structures.

The first sliding mechanisms also are configured and arranged so that the scissors mechanisms translate, translation-2, responsive to forces or torque applied to a portion of the first sliding mechanism. In particular embodiments, the first sliding mechanism includes a rotating portion that causes the scissors mechanism and/or the threaded structures to translate in a direction that is essentially orthogonal to the direction of translation-1 responsive to rotation of the rotating portion.

Each of the two threaded structures is threaded down its' core. Each of these structures assembles directly onto a respective threaded rod of the base unit by being threaded over it. In further embodiments, each of the two threaded structures is a tubular structure. In yet further embodiments, a top portion of the threaded structure is configured and arranged so that it can be rotated about its long axis, whereby the primary device is movable up or down with respect to the base unit. In yet further embodiments, the primary device further includes a wrench that causes such rotation to occur.

Each of the first sliding mechanisms is configured so as to constrains the 'X' configured rods of the scissors mechanism to the threaded structures. Each of the first sliding mechanisms slides over and along an outside surface of a respective threaded structure and in further embodiments is configured and arranged so each first sliding mechanism can slide up and down along the outside of the threaded structure essentially without impediment.

Each of the support portions are configured and arranged so as to fix a respective threaded structure of the translation device to the 'X' configured rods comprising the scissors mechanism. More specifically, the support portions are configured and arranged so that the relationship of this piece to the respective threaded structures does not change.

As indicate herein, such a configuration allows a user to spin or rotate the threaded structure with a wrench or the like in a clockwise or counterclockwise fashion and thereby translate the 'X' or scissors mechanism up or down along the base unit, without changing the dimensions of the 'X', consequently the distance between the two threaded of the base unit does not change. Thus, Translation-2 does not change with this maneuver.

The portion of the device that controls Translation-2 is made of a 1 DOF scissor mechanism and includes two identical nut assemblies. These two nut assemblies connect the other side of the 'X' configuration to the threaded rod of the base unit. Each nut assembly includes two portions: one portion that threads over the threaded rod of the base unit and the second portion that attaches to the 'X', more specifically to an end of the 'X'.

The threaded portion includes a rotating portion, such as a hexagonal nut, at one end which allows a wrench to turn the rotating portion and move it along the threaded rod. The portion that attaches to the 'X' is connected in such a way that it does not rotate with 'X' and also does not constrain the "X'. This translational device is assembled by threading the two nut assemblies over the threads of the threaded rod. These in turn are connected to the 'X' portion of the device.

Translation-2 is achieved by turning the rotating portion that is furthest from the respective foot link of the base unit. The nut assembly closest to the foot link is not moved, and fixes the bottom of the 'X' to a fixed distance from the foot link, thus allowing Translation-2 to change without affecting Translation-1.

In further embodiments, the two rotary joints of each nut assembly are configured and arranged so as to include ball bearings this, however, shall not be construed as limiting the rotary joints to use of only ball bearings. This mechanism locks the translation along the axis of rotation and maintains rigidity through the system. The ball bearings also reduce the internal friction of the mechanism and its play in the joints.

According to another aspect of the present invention there is featured an implant system embodying such a reduction instrument or device described herein and a spinal implant as is known to those skilled in the art. In further embodiments, the spinal implant is operably coupled to the reduction instrument.

In exemplary, illustrative embodiments, the primary device or reduction instrument is mounted via the footlink to a DePuy Expedium Viper V2 extension and Expedium pedicle screw. The Expedium pedicle screw is a polyaxial screw, and during normal function, becomes rigid when locked to a rod in a rod screw construct. It becomes rigid by the construct rod being forced by a nut into a bushing which results in the ball at the head of the screw being forced against the tulip of the screw, and thus by friction, constrains the screw. This mechanism can be engaged with the vertebral body reduction instrument.

One of the components of the vertebral body reduction instrument is a Monolock rod that is composed of a long rod, with a threaded component at its proximal end. It can be placed through the threaded rod of the vertebral body reduction instrument and through the Expedium Viper V2 extension into the Expedium pedicle screw head. The threads at the proximal portion of the Monolock rod engage the threaded rod, and then push the bushing of the DePuy expedium screw into the ball of the screw, and thus lock the ball of the screw against the screw tulip. This in turn constrains the polyaxial head of the screw.

It should be recognized that while the foregoing describes the system according to the present invention being used with the Depuy Expedium/V2 Viper system, this is exemplary. In addition to use with the Depuy Expedium/V2 Viper system, the system of the present invention, in particular the Monolock, works with all existing polyaxial pedicle screw systems, from any manufacture, to convert a polyaxial screw to a functionally a monoaxial screw.

According to further aspects, the present invention also feature methods for stabilizing a spine using such an implant system and/or reduction instrument/device as described herein. Also featured are methods for treating spondylolithesis using surgical techniques and using the reduction instrument and/or implant system of the present invention. Such methods are usable with both "open" surgical procedures and percutaneous pedicle screw techniques. Such methods further includes continuous adjustment and manipulation of the vertebral segment to occur with intuitive uncoupled motion.

As the reduction instrument of the present invention embodies a mechanism or foot link for coupling the instrument to any currently available spinal implant utilizing a plurality of vertebral anchors as the implant, such a reduction instrument is easily adaptable to use such an implant. Thus, a reduction instrument of the present invention would not require redesign of a current implant or vertebral anchor.

Other aspects and embodiments of the invention are discussed below.

DEFINITIONS

The instant invention is most clearly understood with reference to the following definitions:

As used in the specification and claims, the singular form "a", "an" and "the" include plural references unless the context clearly dictates otherwise.

As used herein, the term "comprising" or "including" is intended to mean that the compositions, methods, devices, apparatuses and systems include the recited elements, but do not exclude other elements. "Consisting essentially of", when used to define compositions, devices, apparatuses, systems, and methods, shall mean excluding other elements of any essential significance to the combination. Embodiments defined by each of these transition terms are within the scope of this invention.

USP shall be understood to mean U.S. Patent Number, namely a U.S. patent granted by the U.S. Patent and Trademark Office.

US Publication No. shall be understood to mean U.S. Patent Application Publication No., namely the publication numbered assigned by the USPTO to a published U.S. Non-provisional Patent Application.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

DESCRIPTION OF THE PREFERRED EMBODIMENT

Figure 1:
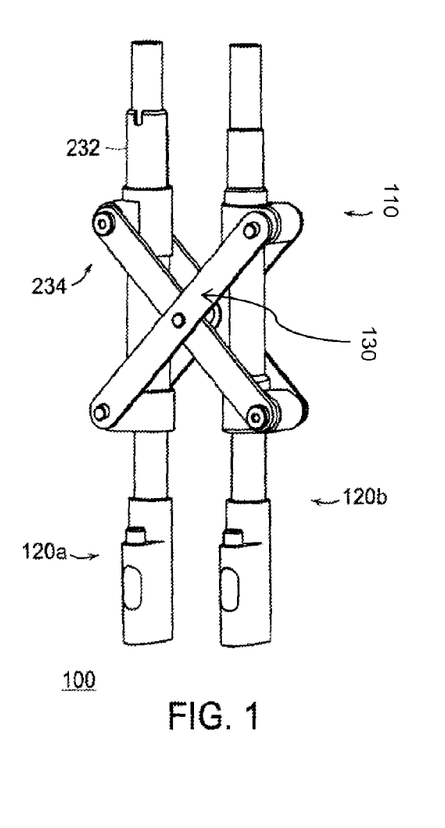
FIG. 1 is an illustrative view of a reduction instrument of the present invention.

Referring now to the various figures of the drawing wherein like reference characters refer to like parts, there is shown in FIG. 1 an illustrative view of a reduction instrument 100 of the present invention. Reference also should be made herein to FIG. 2 which depicts a schematic view of an exemplary reduction instrument and further illustrating the orthogonal translations capable by such a reduction instrument. In particular reference should be made to FIG. 2 when reference is made herein to Translation-1 and Translation-2.

Such a reduction instrument 100 or reduction device includes one or more, more particularly a plurality of modules 110 each module including a base unit 120 having two base elements and a primary device 130. The base 120, more specifically the base elements thereof are configured and arranged so as attach to a plurality of vertebral anchors and the primary device 130 controls the orthogonal translations. The vertebral anchors are any of a number of vertebral anchors as are known to those skilled in the art (e.g., spinal pedicle screw instrumentation) or hereinafter developed. As described further herein in connection with FIGS. 6-7, in further illustrative, exemplary embodiments the base unit 120 is configured and arranged such that it can mate with the Depuy Expedium pedicle screw instrumentation system through the Viper V2 percutaneous extensions.

As the reduction instrument and functionalities thereof are intended for use with a body, the materials shall be any of a number of bio-compatible materials presently known or hereinafter developed. Such materials also shall be suitable for the forces and loads that can occur during usage of the instrument. In addition, while particular shapes or geometries are described herein, it is within the scope of the present invention for other shapes or geometries to be used as long as the described functional can be carried out using such shapes or geometries.

Figure 2:
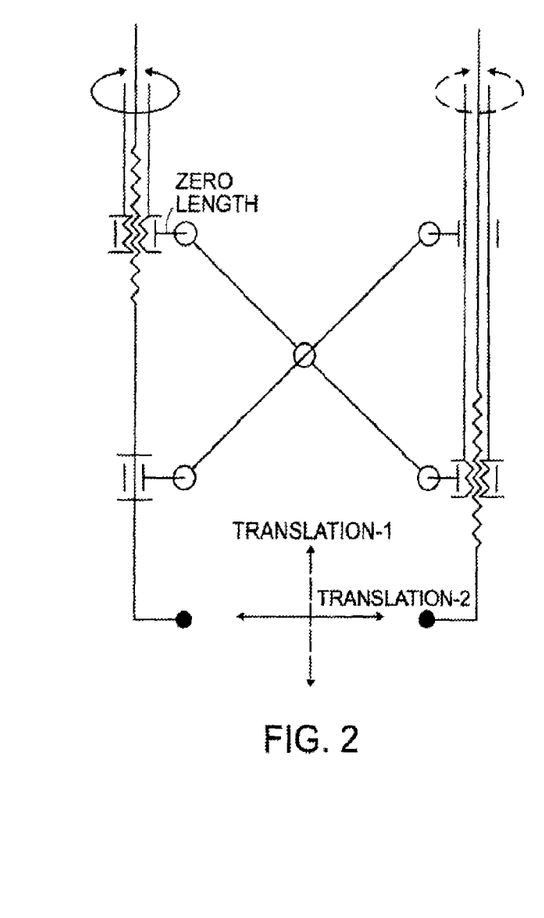
FIG. 2 is a schematic view of an exemplary reduction instrument and further illustrating the orthogonal translations capable by such a reduction instrument.

The modules 110 for such a reduction instrument 100 are configured and arranged as needed for correcting the deformity. As described in further detail herein, each module has two degrees of freedom (DOF) with uncoupled orthogonal translations. Such a reduction instrument, allows the reorientation of the vertebral segment as needed via uncoupled orthogonal translations as shown in FIG. 2. Thus, distraction/compression and translation of the vertebral bodies can be achieved over a defined spinal segment, where uncoupling of this action allows intuitive and controlled correction of a deformity.

Such a reduction instrument or device is unique in that it usable in combination with almost any of a number of currently available vertebral anchors (e.g., spinal pedicle screw instrumentation). It also is usable with both "open" surgical procedures and percutaneous pedicle screw techniques. It allows for continuous adjustment and allows for manipulation of the vertebral segment to occur with intuitive uncoupled motion.

Figure 3:
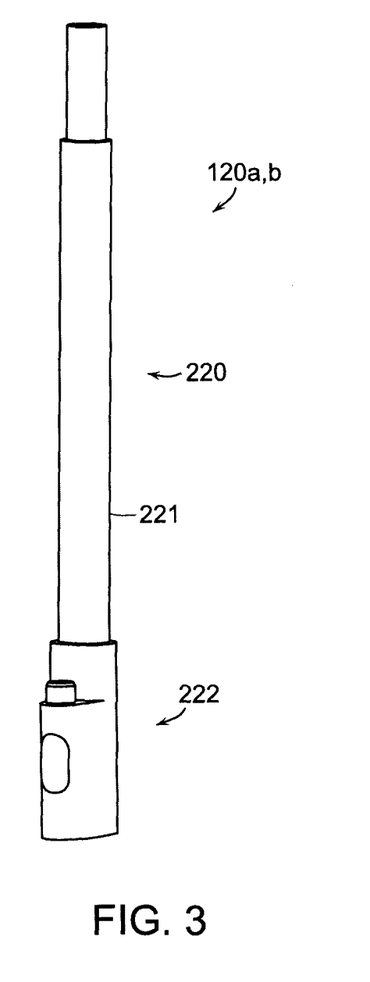
FIG. 3 is a illustrative view of a base unit according to the present invention

In further embodiments, and with additional reference to FIG. 3, each base unit 120a,b includes two base elements including a threaded rod portion 220 and a foot link 222 at one end of the threaded rod portion. The foot link 222 is configured and arranged so it will mate with any of a number of spinal implants as is known to those skilled in the art, preferably spinal implants embodying spinal pedicle screw instrumentation.

The threaded rod portion 220 is threaded along its length and about the outside surface 221. In further embodiments, such a rod portion 220 is a tubular shaped member. The thread pitch of the threaded rod portion 220 is established to corresponds to or complement the same thread pitch as that embodied in the threaded structure 302 of the primary device 130 (see FIG. 4A). In this way, the primary device 130 is threaded onto the threaded rod portion 220. In yet further embodiments, the thread pitch lends a mechanical advantage that allows the relative movement of the vertebral bodies.

In further embodiments, the primary device 130 includes two portions that are connected to one another by two parallel sets of bars or rods 301 forming a scissors mechanism 234, the sets of bars are allowed to pivot in one plane around a central point forming a double 'X' configuration. The primary device 130 also is configured and arranged so as to separately control both orthogonal translations, Translation-1 and Translation-2, that is provided by the primary device 130 as depicted in FIG. 2.

Depending how many and how the one or more modules are configured, placed, and oriented on the spine, the two translations or two DOF for each module can achieve a multi-degree of freedom correction. These can be used to correct distraction/compression and anterior/posterior translation. In a typical mounting situation, Translation-1 is aligned along the anterior/posterior translational direction and Translation-2 along the distraction/compression direction.

Such a primary device 130 also includes a first translation mechanism 300 (see FIG. 4A and FIG. 5A), that allows translation along the length of the rod portion 220 of each base unit 120a,b. Such a first translation mechanism 300 includes one threaded structure 302 that threadably engages a threaded rod portion 220 of the base unit, a first sliding mechanism 304 that slidably couples the scissors mechanism and the threaded structure and a support portion 306 that operably couples the scissors mechanism and the threaded structures. While a threaded connections are described herein, it is within the scope of the present invention to utilize any of a number of mechanical connections as are known to those skilled in the art, which can create friction between two objects such that one object can be moved relative to the other object.

Figure 5A:
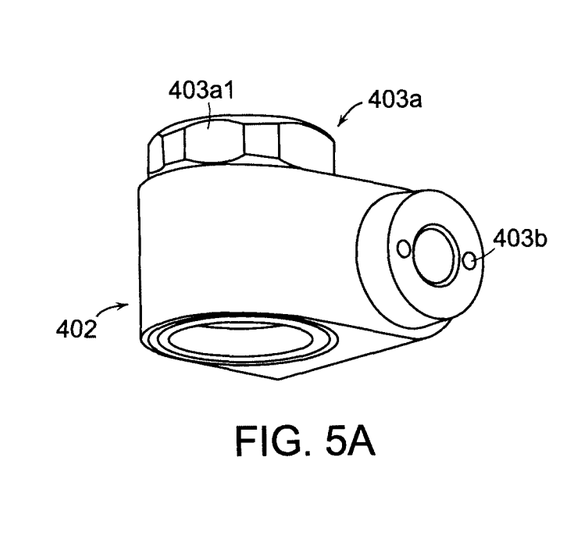
FIGS. 5A, B are illustrative views of the nut assemblies of the present invention.
Figure 5B:
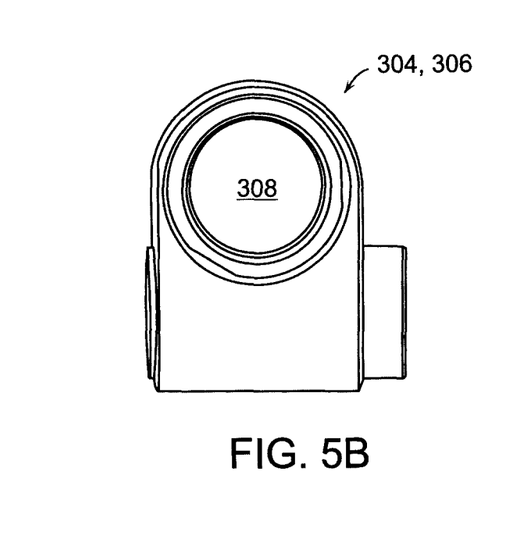

The threaded structure 302 is threaded down through a threaded through aperture 308 (see FIG. 5B) at the core of the structure. The threaded structure is assembled directly onto the respective threaded rod portion 220 of the base unit by being threaded over it. In further embodiments, the threaded structure 302 is a tubular structure.

In yet further embodiments, a top portion of a threaded structure 302 is configured and arranged so that it can be rotated about its long axis (see FIG. 2) whereby the primary device is movable up or down with respect to the base unit—Translation-1. In yet further embodiments, the primary device further includes a wrench that engages the threaded structure so as to cause such rotation to occur.

Figure 4A:
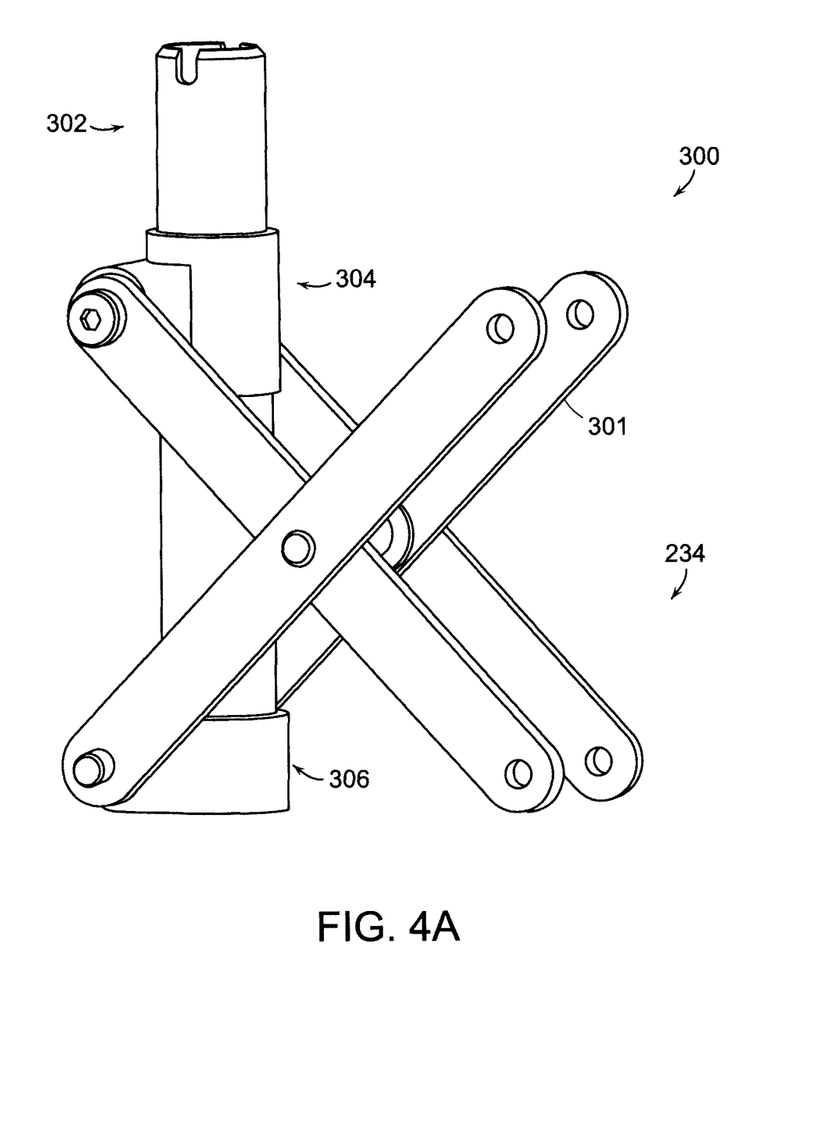
FIG. 4A is an illustrative view of a portion of a reduction instrument to show one translation capability of the present invention.

The first sliding mechanism 304 is configured and arranged so as constrains the 'X' configured rods 301 of the scissors mechanism 234 to the respective threaded structure 302. The first sliding mechanism also is configured and arranged so it slides over and along an outside surface of a respective threaded structure 302 and in further embodiments is configured and arranged so the first sliding mechanism can slide up and down along the outside of the threaded structure 320 essentially without impediment.

The sliding mechanism 304 also is configured and arranged so that the scissors mechanisms translate, Translation-2, responsive to forces or torque applied to a portion of the sliding mechanism. In particular embodiments, the first sliding mechanism includes a rotating portion that causes the scissors mechanism and/or the threaded structures to translate in a direction that is essentially orthogonal to the direction of Translation-1 responsive to rotation of the rotating portion.

The support portion 306 is configured and arranged so as to fix the respective threaded structure 302 of the translation device or mechanism 300 to the 'X' configured rods 301 comprising the scissors mechanism. More specifically, the support portion 306 is configured and arranged so that the relationship of this piece to the respective threaded structures does not change.

As indicate herein, such a configuration allows a user to spin or rotate the threaded structure 302 with a wrench or the like in a clockwise or counterclockwise fashion and thereby translate the 'X' or scissors mechanism 234 up or down along the base unit 120a without changing the dimensions of the 'X', consequently the distance between the two threaded of the base unit does not change. In this way, Translation-2 does not change with this maneuver (i.e., the configuration of the rods 301 is not altered).

Figure 4B:
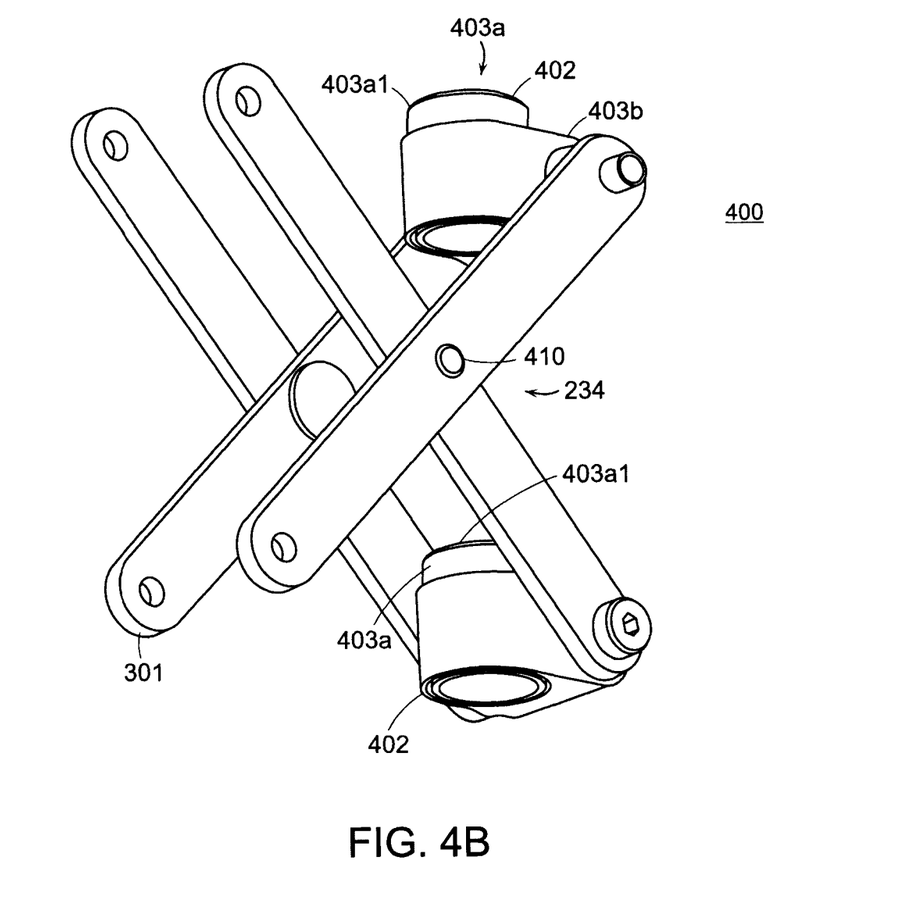
FIG. 4B is an illustrative view of a portion of a reduction instrument to show another translation capability of the present invention.

Now with reference to FIG. 4B, the portion 400 of the primary device that controls Translation-2 is made of a 1 DOF scissor mechanism 234 and includes two nut assemblies 402. It should be noted that components appearing in both FIGS. 4A,B are numbered identically.

The two nut assemblies 402 or components connect the other side of rods 301 comprising the 'X' configuration to the threaded rod 220 of the respective base unit 120b. Each nut assembly 402 includes two portions: one portion 403a threads over the threaded rod 220 of the respective base unit 120b and the second portion 403b attaches to the 'X', more specifically, to an end of the 'X' using any of a number of techniques known to those skilled in the art.

The threaded portion 403a includes a rotating portion 403a1, such as a hexagonal nut, at one end which allows a wrench to turn the rotating portion and move it along the threaded rod. The second portion 403b that attaches to the 'X' is connected in such a way that it does not rotate with 'X' and also does not constrain the "X' from moving with respect to itself (i.e., the sets of rods rotate about the central point 410).

This translational device 400 is assembled by threading the two nut assemblies 402 over the threads of the threaded rod 220. The two nut assemblies are in turn are connected to the 'X' portion 234 (i.e., to corresponding ends of the rods 301 making up the 'X' portion).

Translation-2 is achieved by turning the rotating portion 403a1 that is furthest from the foot link 222 of the respective base unit 120b. The nut assembly 402 closest to the foot link is not moved, and fixes the bottom of the 'X' to a fixed distance from the foot link, thus allowing Translation-2 to change without affecting Translation-1.

In further embodiments, the two rotary joints 403a of each nut assembly 400 are further configured and arranged so as to include ball bearings. This mechanism locks the translation along the axis of rotation and maintains rigidity through the system. The ball bearings also reduce the internal friction of the mechanism and its play in the joints.

According to another aspect of the present invention there is featured an implant system embodying such a reduction instrument or device described herein and a spinal implant as is known to those skilled in the art. In further embodiments, the spinal implant is operably coupled to the reduction instrument.

Figure 6:
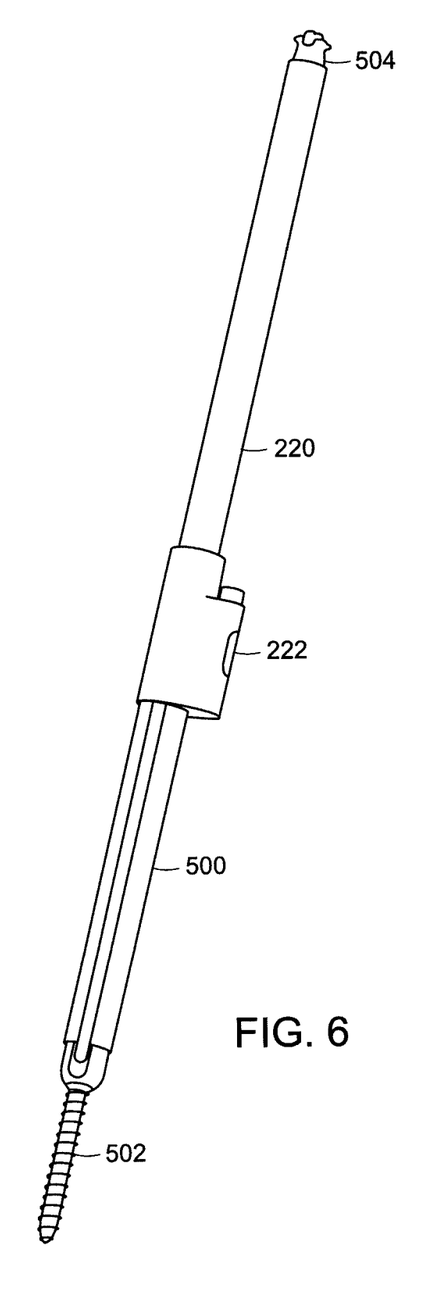
FIG. 6 is an illustrative view of a base unit being coupled to a portion of a spinal implant, which in combination with a reduction instrument of the present invention forms an implant system.
Figure 7A:
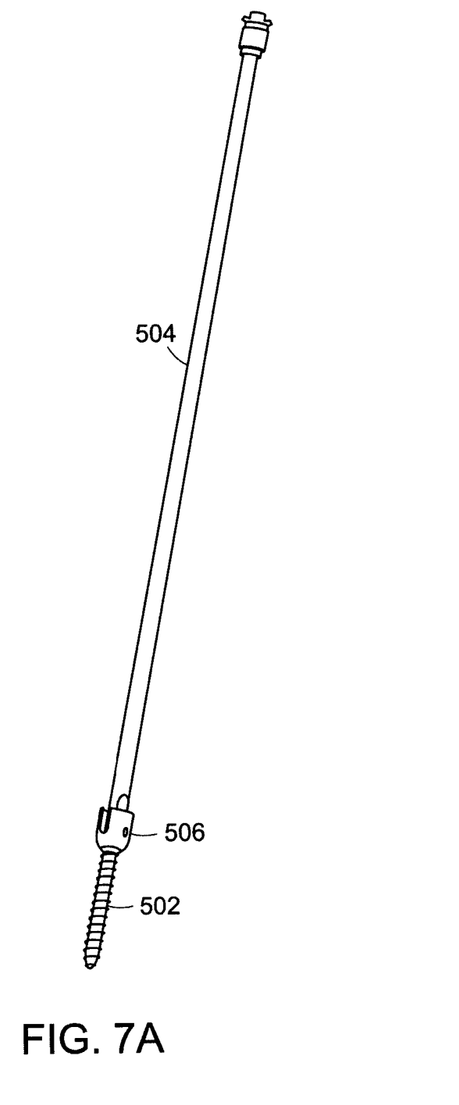
FIGS. 7A, B are illustrative views of portions of features (e.g., the Monolock) shown in FIG. 6.
Figure 7B:
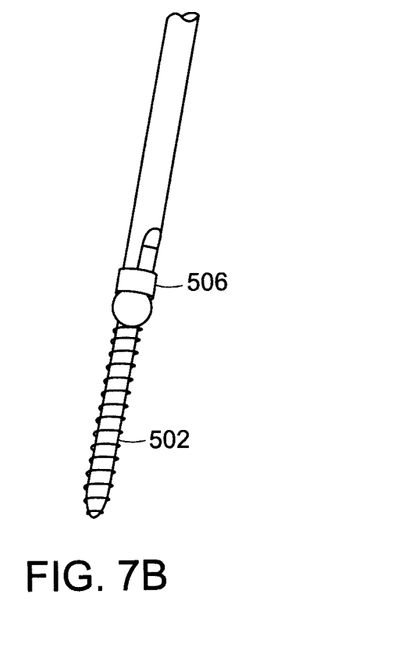

In exemplary, illustrative embodiments and with reference to FIGS. 6-7, the primary device or reduction instrument is mounted via the footlink 222 to a DePuy Expedium Viper V2 extension 500 and Expedium pedicle screw 502. The Expedium pedicle screw 502 is a polyaxial screw, and during normal function, becomes rigid when locked to a rod in a rod screw construct. It becomes rigid by the construct rod being forced by a nut into a bushing which results in the ball at the head of the screw being forced against the tulip of the screw, and thus by friction, constrains the screw. This mechanism can be engaged with the vertebral body reduction instrument.

One of the components of the vertebral body reduction instrument according to this embodiment is a Monolock rod 504 that is composed of a long rod, with a threaded component 506 at its proximal end. It can be placed through the threaded rod 220 of the vertebral body reduction instrument 100 and through the Expedium Viper V2 extension 500 into the head of the Expedium pedicle screw 502. The threads at the proximal portion of the Monolock rod engage the threaded rod, and then push the bushing of the DePuy expedium screw into the ball of the screw, and thus lock the ball of the screw against the screw tulip. This in turn constrains the polyaxial head of the screw.

It should be recognized that the Monolock can be adapted for use with any of a number of pedicle screw systems as are known to those skilled in the art. Thus, the foregoing discussion shall not be construed as limiting usage of the Monolock to only the above-described exemplary, illustrative embodiment.

As the reduction instrument of the present invention embodies a mechanism or foot link for coupling the instrument to any of a number of currently vertebral anchors, such as those embodying a utilizing polyaxial screw, such a reduction instrument is easily adaptable to use such a vertebral anchor.

According to further aspects, the present invention also feature methods for stabilizing a spine using such an implant system and/or reduction instrument/device as described herein. Also featured are methods for treating spondylolithesis using surgical techniques and using the reduction instrument and/or implant system of the present invention. Such methods are usable with both "open" surgical procedures and percutaneous pedicle screw techniques. Such methods further includes continuous adjustment and manipulation of the vertebral segment to occur with intuitive uncoupled motion.

Such methods include providing one or more modules comprising any of the above described reduction instruments 100 and localizing the one or more modules to a spinal implant and securing the reduction instrument to the spinal implant. Thereafter the first translation mechanism 300 is appropriately manipulated so as to cause the scissors mechanism 234 to move in either direction of Translation-1 and/or the second translation mechanism 400 is appropriately manipulated so as to cause movement in either direction of Translation-2, thereby causing the rods 301 to pivoting motion about the central point. As these first and second translation mechanisms 300, 400 are uncoupled the movement in one translation direction (e.g., Translation-1) do not lead to movement in the other translation direction (e.g., Translation-2).

In further embodiments, such methods further include performing other surgical techniques related to the surgical treatment of the underlying condition. Such other surgical techniques include fusion of adjacent vertebrae, bone grafting, discotomy, decompression or laminectomy and spinal implants. Additionally such methods for treating further includes wound care and minimizing onset of infection.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A reduction instrument comprising:
   at least one module comprising a base unit and a primary device;
   the base unit comprising a first base element and a second base element arranged in parallel, the first and second base elements each having a fixed length rod portion having an attachment end configured to attach to one or more vertebral anchors; and
   the primary device comprising a first movable structure that engages a first fixed length rod portion of the first base element, and a second movable structure that engages a second fixed length rod portion of the second base element, and a scissors mechanism connecting the first and second movable structures,
   wherein movement of the first movable structure causes translation of the primary device in one direction along a length of the first base element via the first fixed length rod portion and the second fixed length rod portion, and wherein the scissors mechanism independently causes translation of the primary device in a second direction, the first and second directions being orthogonal to each other.

2. The reduction instrument of claim 1, wherein the rod portion of the first and second base elements comprise a threaded portion, and wherein the first movable structure and the second movable structure are threaded movable structures that engage the threaded portion of the first and second base elements.

3. A method for surgical treatment of spondylolithesis comprising the step(s) of:
   providing the reduction instrument of claim 1, wherein each of the at least one modules is configured and arranged to cause translation of a vertebral segment in a first direction and a second direction, the first and second directions being orthogonal to each other;
   manipulating the reduction instrument in either or both of the first and second directions so as to correct for translation and to apply distraction across a segment in an independent fashion.

4. The surgical treatment method of claim 3, further comprising the step(s) of:
   securing the reduction instrument to a spine using spinal pedicle screw instrumentation.

5. The surgical treatment method of claim 3, further comprising the step(s) of:
   aligning the reduction instrument with respect to a spine so that the first direction is aligned along an anterior/posterior translational direction and so that the second direction is along a distraction/compression direction.

6. The surgical treatment method of claim 3, further comprising the step(s) of:
   reorienting a vertebral segment via uncoupled translations in one or both of the first and second directions.

7. A surgical reduction instrument comprising:
   at least one module, where each module includes a base unit and a primary device, the base unit being operably coupled to the primary device;
   wherein the primary device is configured and arranged to reorient a vertebral segment using uncoupled orthogonal translations to perform distraction/compression and translation of vertebral bodies comprising the vertebral segment;
   wherein the base unit comprises a first base element and a second base element arranged in parallel, the first base element and the second base element each including a fixed length rod portion having an attachment end configured to attach to one or more vertebral anchors;
   wherein the primary device comprises a first portion that is movably mounted along the fixed length rod portion of the first base element, a second portion that is movably mounted along the fixed length rod portion of the second base element, and at least two bars that are configured and arranged so as to form a scissors mechanism extending between the first portion and the second portion,
   wherein the first and second portions of the primary device are movably mounted along the fixed length rod portions of the first and second base elements such that the scissors mechanism is translatable upwards and downwards along a length of the fixed length rod portions thereby adjusting the primary device without changing dimensions of the scissors mechanism.

8. The surgical reduction instrument of claim 7, wherein the scissors mechanism comprises two parallel sets of bars, the parallel sets of bars being further arranged so that they can pivot in one plane around a central point.

9. The surgical reduction instrument of claim 7, wherein the attachment end includes a threaded portion and a foot link, the foot link being configured and arranged so as to mate with the one or more vertebral anchors.

10. The surgical reduction instrument of claim 9, wherein:
    the primary device further comprises:
    a sliding mechanism that slidably couples one end of the scissors mechanism and the threaded structure, and
    a support portion that operably couples the scissors mechanism and the primary device threaded structure,
    wherein the sliding mechanism includes a threaded structure that threadably engages the threaded portion of the base unit, and wherein the threaded structure is threaded over the base unit threaded portion.

11. The surgical reduction instrument of claim 10, wherein the threaded structure is configured and arranged so that rotation about its long axis causes the scissors mechanism to be movable with respect to the base unit.

12. The surgical reduction instrument of claim 10, wherein:
    the first and second portions of the primary device comprise two nut assemblies, wherein the two nut assemblies connect to a second end of the scissor mechanism; and
    wherein each nut assembly includes a first portion that is movably mounted along the rod portion of the second base element.

13. The surgical reduction instrument of claim 12, wherein:
    the rod portion of the second base element is threaded and the nut assembly first portion includes a rotating portion at one end thereof, where manipulation of the rotating portion to cause the nut assembly to move along the threaded rod portion of the second base element.

14. The surgical reduction instrument of claim 13, wherein: each nut assembly includes a second portion that is secured to the scissors mechanism such that it does not rotate with the scissors mechanism.

15. The reduction instrument of claim 12, wherein the second movable structure comprises two threaded nut assemblies.

* * * * *